US00PP16297P3

(12) United States Plant Patent

Iwaki et al.

(10) Patent No.: US PP16,297 P3

(45) Date of Patent: Feb. 28, 2006

(54) *PETUNIA* PLANT NAMED 'SUNPATIKI'

(50) Latin Name: *Petunia hybrida*
Varietal Denomination: Sunpatiki

(75) Inventors: Kazunari Iwaki, Omihachiman (JP); Takuro Ishihara, Higashikurume (JP); Shinya Miyano, Katori-gun (JP)

(73) Assignees: Suntory Flowers Limited, Tokyo (JP); Keisei Rose Nurseries, Inc., Tokyo (JP)

( * ) Notice: Subject to any disclaimer, the term of this patent is extended or adjusted under 35 U.S.C. 154(b) by 87 days.

(21) Appl. No.: 10/811,241

(22) Filed: Mar. 25, 2004

(65) Prior Publication Data

US 2005/0216999 P1 Sep. 29, 2005

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP9,322 | P | 10/1995 | Tachibana et al. |

OTHER PUBLICATIONS

U.S. Appl. No. 10/611,359, filed Jun. 30, 2003, Miyazaki et al.

Suntory Flowers Ltd., "Flower & Green, the newest catalog 2004" Published 2003, with Explanation for IDS Document.

Jackson & Perkins Wholesale, Inc., USA, "The 2004 Suntory Collection" Published 2003, with Explanation for IDS Document.

Pineae Greenhouses, Inc., USA, "Pineae Peak Performers featuring the 2004 Suntory Collection" Published 2003, with Explanation for IDS Document.

Goldsmith Seeds, Inc., USA, "Goldsmith Seeds 2003–2004 Catalog" Published 2003, with Explanation for IDS Document.

Sakata Seeds Co., Japan, "Katei Engei, 2004 Spring" Published 2003, with Explanation for IDS Document.

Fukukaen Nursery & Bulb Co., Ltd., Japan, "Fukukaen Flower Catalogue for Gardening Farm, Autumn '98 to Spring '99" Published 1997, with Explanation for IDS Document.

Fukukaen Nursery & Bulb Co., Ltd., Japan, "Fukukaen Flower Catalogue for Gardening Farm, Autumn 2003 to Spring 2004" Published 2002, with Explanation for IDS Document.

Dai–ichi Seed Co., Ltd., Japan, "Dai–ichi Seed Co., Ltd. Catalogue for Gardening Farm, Summer 2000 to Spring 2001" Published 1999, with Explanation for IDS Document.

*Primary Examiner*—Kent Bell
(74) *Attorney, Agent, or Firm*—Christie, Parker and Hale, LLP

(57) ABSTRACT

Disclosed herein is a new and distinct variety of *Petunia* plant having a decumbent habit and short stems. The *Petunia* plant has abundant branching, and a great profusion of blooms, the whole plant remaining in bloom for a considerable period of time. The flowers are single and small, the petals having pale yellow-green with brilliant yellow-green and brilliant greenish-yellow veins. The inside color of the corolla throat is brilliant greenish-yellow and the outside of the corolla tube is light yellow-green. The plant exhibits high resistance to rain, heat, cold and disease.

2 Drawing Sheets

Botanical/commercial classification: *Petunia hybrida*/*Petunia* Plant.

Varietal denomination: cv. 'Sunpatiki'.

BACKGROUND OF THE VARIETY

The present invention relates to a new and distinct variety of *Petunia* plant, which originated from the crossing of a *Petunia* hybrid variety called '152-3' (unpatented) as the female parent and a seedling called 'Summer Sun' (unpatented) as the male parent.

The *Petunia* is a very popular plant that is used for flower bedding and potting in the summer season. There are only a few *Petunia* varieties that do not have an upright growth habit and that have a high resistance to rain, heat, and disease. *Petunias* of the 'Revolution' series include 'Revolution Purple pink' (U.S. Plant Pat. No. 6,915), 'Revolution Brilliant pink' (U.S. Plant Pat. No. 6,914), 'Revolution Brilliantpink-Mini' (U.S. Plant Pat. No. 6,899), and 'Revolution Blue vein' (U.S. Plant Pat. No. 9,322). These are decumbent type plants having long stems, a lower plant height, abundant branching, and a high resistance to heat, rain and disease. Likewise, there are only a few *Petunia* varieties having a great profusion of small size flowers, yellow colored flower petals and a high resistance to rain, heat, and diseases. Accordingly, this invention was aimed at obtaining a new *Petunia* variety having yellow colored petals, together with the above features.

Progress

The female parent '152-3' used in the crossing of 'Sunpatiki' is a strain of our breeding lines, having a spreading growth habit with many branches. It has very small single flowers, the petals having yellowish white color.

The male parent 'Summer Sun' used in the crossing of 'SunPatiki' is a cultivar having an erect growth habit with very few branches, and thick stems. It has large vivid yellow flowers. The seed of 'Summer Sun' is commercially available.

In January 2000, crossing of '152-3' as the female parent and 'Summer Sun' as the pollen parent was conducted at Yokaichi-shi, Shiga-ken, Japan. In May 2000, 60 seedlings were obtained from that crossing. These seedlings were grown in pots in glasshouses and were evaluated. One seedling was selected in view of its growth habit, flower size and color in September 2000. That seedling was propagated by cutting and a trial was carried out by flower potting and bedding from April to September 2001 at Yokaichi-shi, Shiga-ken, Japan. The botanical characteristics of that plant were then examined, using similar varieties 'Sunpatire' (U.S. Ser. No. 10/611,359) and 'Fantasy Crystal Red' (unpatented) for comparison. As a result, it was concluded that this *Petunia* plant is distinguishable from any other variety whose existence is known to us, and is uniform and stable in its characteristics. The new variety of *Petunia* plant was named 'Sunpatiki'.

In the following description, the color-coding is in accordance with the Horticultural Colour Chart of The Royal Horticultural Society, London, England (R.H.S. Colour Chart).

SUMMARY OF THE VARIETY

This new variety is unlike any *Petunia* commercially available as evidenced by the following unique combinations of characteristics.

1. Spreading growth habit with short stems.
2. Abundant branching and a great profusion of blooms.
3. The flowers are single and small. The petal color is pale yellow green (near R.H.S.1D) with brilliant yellow green (near R.H.S.151C) and brilliant greenish-yellow (near R.H.S. 7B) venation.
4. The plant has a high resistance to rain, cold, heat and disease.

The new variety 'Sunpatiki' differs from the similar variety 'Sunpatire' in the following points.

1. The leaf shape of 'Sunpatiki' is elliptic, while that of 'Sunpatire' is lanceolate.
2. The leaf of 'Sunpatiki' is smaller and thinner than that of 'Sunpatire'.
3. The petal color of 'Sunpatiki' is pale yellow green (near R.H.S.1D) with brilliant yellow green (near R.H.S.151C) and brilliant greenish yellow (near R.H.S.7B) venation, while that of 'Sunpatire' is vivid red (near R.H.S.N57A).
4. The apex shape of petal of 'Sunpatiki' is truncate while that of 'Sunpatire' is rounded.

The new variety 'Sunpatiki' differs from the similar variety 'Fantasy Crystal Red' in the following points.

1. The growth habit of 'Sunpatiki' is spreading, while that of 'Fantasy Crystal Red' is erect.
2. The stem length of 'Sunpatiki' is shorter than that of 'Fantasy Crystal Red'.
3. The leaf of 'Sunpatiki' is thinner than that of 'Fantasy Crystal Red'.
4. The petal color of 'Sunpatiki' is pale yellow green (near R.H.S.1D) with brilliant yellow green (near R.H.S.151C) and brilliant greenish yellow (near R.H.S. 7B) venation, while that of 'Fantasy Crystal Red' is vivid red (R.H.S. 52A) with strong red (R.H.S.53C) venation.
5. The apex shape of petal of 'Sunpatiki' is truncate, while that of 'Fantasy Crystal Red' is obtuse.
6. The heat resistance of 'Sunpatiki' is stronger than that of 'Fantasy Crystal Red'.

The new variety of *Petunia* plant 'Sunpatiki' was asexually reproduced by use of cutting at Yokaichi-shi, Shiga-ken, Japan, and the homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during July 2003 while cultivating under the trial field in 15 cm pots at an age of approximately 6 months at Yokaichi-shi, Shiga-ken, Japan.

DESCRIPTION OF THE VARIETY

Figure 1:
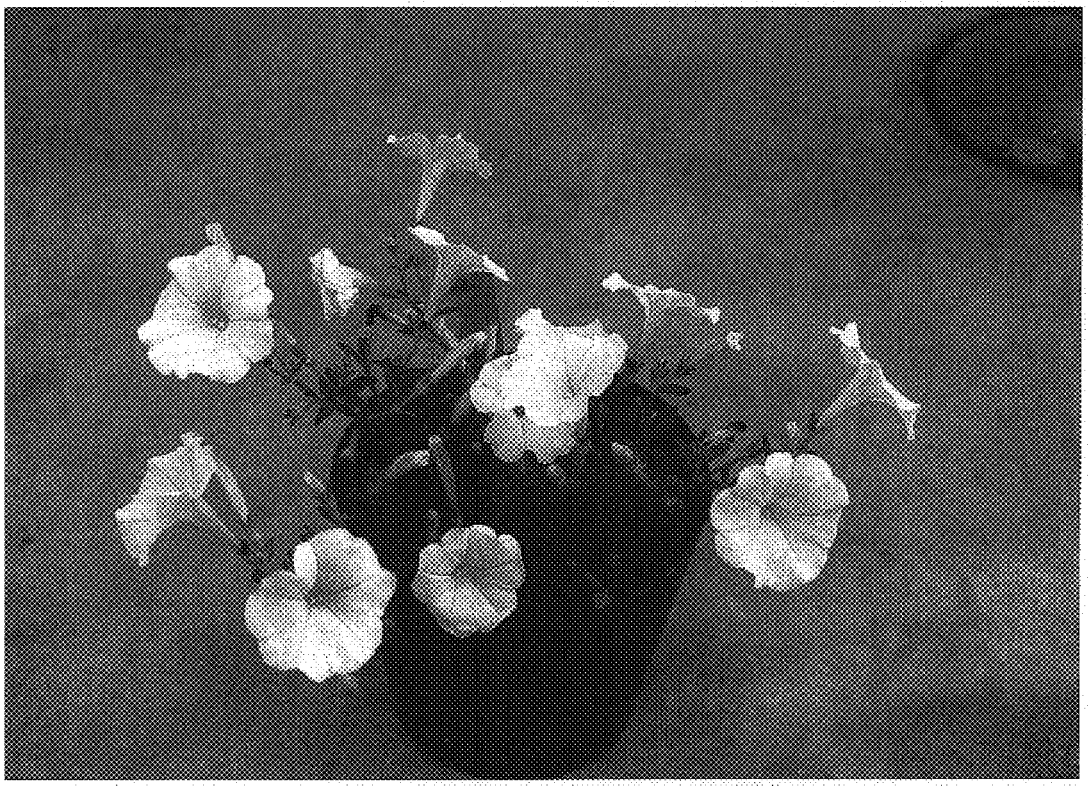
FIG. 1 is a photograph of a typical plant of the new variety of *Petunia* plant 'Sunpatiki' while growing in a pot.
Figure 2:
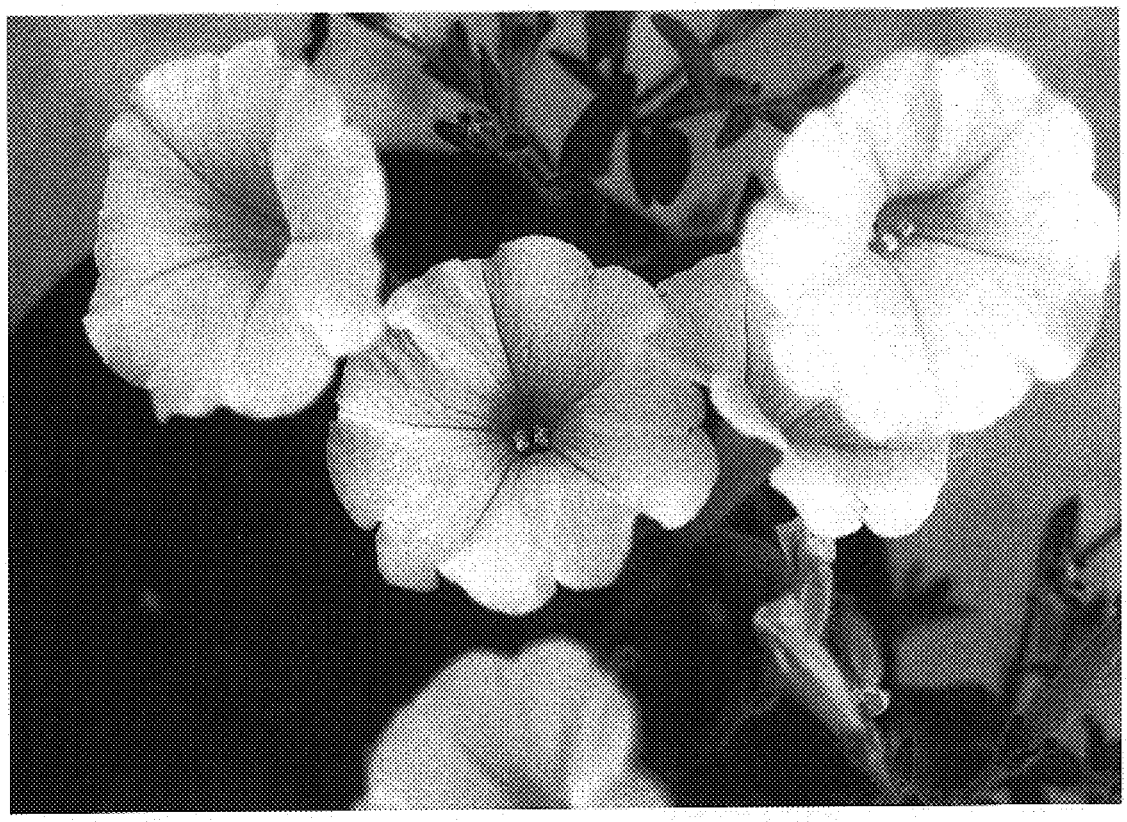
FIG. 2 is a close view of flowers and leaves of the new variety of *Petunia* plant 'Sunpatiki'.

The botanical characteristics of the new and distinct variety of *Petunia* plant named 'Sunpatiki' are as follows when observed during July at Yokaichi-shi, Shiga-ken, Japan at an age of approximately 6 months.

Plant:

*Growth habit*.—Spreading.
*Plant height*.—Approximately 19 cm.
*Spreading area of plant*.—Approximately 14 cm.
*Blooming period*.—Early April to late October in the southern Kanto area, Japan. The plant shape does not change throughout this period. A typical flower commonly lasts approximately 5 days on the plant when experiencing a temperature of approximately 20° C.

Stem:

*Length*.—Approximately 1.9 cm.
*Thickness*.—Approximately 2.0 mm.
*Pubescence*..—Normal.
*Branching*.—Abundant.
*Internode length*.—Approximately 1.3 cm.
*Color*.—Near R.H.S. 144B (vivid yellow-green).

Leaf:

*Whole shape*.—Elliptic with entire margin. The apex shape is acute, and the base shape is attenuate.
*Length*.—Approximately 2.7 cm.
*Width*.—Approximately 1.7 cm.
*Color*.—Upper side color is near R.H.S. 137A (moderate olive-green). Lower side color is near R.H.S. 146A (moderate yellow-green).
*Thickness*.—Approximately 0.2 mm.
*Pubescence*.—Sparse.

Buds:

*Shape*.—Cylindrical.
*Length*.—Approximately 4.5 cm.
*Diameter*.—Approximately 1.0 cm.
*Color*.—Near R.H.S. 1C with venation near R.H.S. 145B.

Flower:

*Depth*.—Approximately 5.0 cm.
*Tube length*.—Approximately 2.6 cm.

*Throat diameter*.—Distal end: approximately 1.1 cm.
*Tube diameter*.—Proximal end: approximately 4.0 mm.
*Facing direction*.—Slanted upward.
*Type*.—Single.
*Shape*.—Funnel-shaped, with five-fissures.
*Shape of petal tip*.—Truncate.
*Lobation*.—Shallow.
*Waviness of petal*.—Weak.
*Diameter*.—Approximately 4.4 cm.
*Color*.—Petal; near R.H.S. 1D (pale yellow-green) with venation near R.H.S.151C (brilliant yellow green) and near R.H.S.7B (brilliant greenish-yellow). Inside color of the corolla throat, near R.H.S. 7B (brilliant greenish-yellow). Outside color of the corolla tube; near R.H.S. 1C (light yellow-green).

Petals:
*Width*.—Approximately 3.0 cm.
*Length from throat*.—Approximately 2.5 cm.
*Shape*.—Very broadly obovate.
*Margin*.—Entire.
*Texture*.—Smooth.
*Color*.—Lower surface, near R.H.S. 11C with near R.H.S. 11A venation.
*Reproductive organs*.—1 normal pistil and 5 normal stamens. Color of pistil is near R.H.S. 145D (moderate yellow-green). Color of stamen is near R.H.S. 10D (pale yellowish-green).

Peduncle:
*Diameter*.—Approximately 0.9 mm.
*Length*.—Approximately 1.6 cm.
*Color*.—Near R.H.S. 144A.
*Surface*.—Pubescent.
*Calyx*.—Narrow. 5 sepals fused at the base.

Sepals:
*Shape*.—Narrow elliptic.
*Apex shape*.—Rounded.
*Base*.—Fused.
*Margin*.—Entire.
*Surface*.—Pubescent.
*Length*.—Approximately 1.4 cm.
*Width*.—Approximately 4.0 mm.
*Color*.—Upper surface, near R.H.S. 137C, lower surface near R.H.S. 137C.

Physiological and ecological characteristics: High resistance to rain, cold, heat and disease. Moderate resistance to pests.

This new variety of *Petunia* plant is most suitable for flower bedding and potting, particularly in hanging pots or planters. Pinching of old blossoms will enhance the formation of new blossoms.

It is claimed:

1. A new and distinct variety of *Petunia* plant named 'Sunpatiki', substantially as herein illustrated and described.

* * * * *